United States Patent [19]

Onopchenko et al.

[11] 4,139,561
[45] Feb. 13, 1979

[54] NOVEL SUBSTITUTED AMINO-AROMATIC ACETYLENES AND THEIR METHOD OF PREPARATION

[75] Inventors: Anatoli Onopchenko, Monroeville; Edward T. Sabourin, Allison Park; Charles M. Selwitz, Monroeville, all of Pa.

[73] Assignee: Gulf Research & Development Company, Pittsburgh, Pa.

[21] Appl. No.: 881,198

[22] Filed: Feb. 27, 1978

[51] Int. Cl.$^2$ .................... C07C 85/11; C07C 85/24; C07C 91/40

[52] U.S. Cl. .................................. 260/575; 260/571; 260/578; 528/183; 528/345

[58] Field of Search ................ 260/580, 575, 571, 578

[56] References Cited

U.S. PATENT DOCUMENTS

| 3,177,258 | 4/1965 | Rylander et al. ............... 260/580 X |
| 3,928,450 | 12/1975 | Bilow et al. ........................ 260/571 |
| 3,975,444 | 8/1976 | Kovar et al. ....................... 260/571 |
| 4,002,673 | 1/1977 | Braden et al. ................. 260/580 X |

OTHER PUBLICATIONS

Rauss–Godineau, "Chem. Ab.", vol. 66, Ab. No. 75765z, (1967).

Primary Examiner—Winston A. Douglas
Assistant Examiner—John Doll

[57] ABSTRACT

Substituted acetylenes wherein the amino and acetylene groups are directly connected to aromatic ring carbon atoms and wherein the substituted acetylene has at least 3 carbon atoms and a hydroxyl group on the carbon atom adjacent to the acetylene group are claimed as new compositions of matter. The new compositions are prepared by the selective reduction of the corresponding nitroaromatic by contacting the nitroaromatic and free molecular hydrogen with a catalyst consisting essentially of ruthenium. A new process is also described for the preparation of an aminophenylacetylene.

30 Claims, No Drawings

NOVEL SUBSTITUTED AMINO-AROMATIC ACETYLENES AND THEIR METHOD OF PREPARATION

This invention relates to novel amino-aromatic acetylenes and in particular 2-methyl-4-(3-aminophenyl)3-butyn-2-ol, their method of preparation, and a new method for preparing aminophenylacetylene.

BACKGROUND OF THE INVENTION

The recent introduction of acetylene-terminated polyimides to produce cured reaction products which are stable at very high temperatures of 450° C. and up has created an interest and need to produce the polyimides at attractive and competitive costs. The prime difficulty in the preparation of the acetyleneterminated polyimides which are described, for example, in U.S. Pat. No. 3,845,018 and U.S. Pat. No. 3,879,349, both to Norman Bilow et al, is the preparation of the monomers which include in one instance the preparation of meta-aminophenylacetylene (APA). This invention relates to the discovery of certain new intermediates which can be converted to aminophenylacetylene and methods of preparing the new intermediates.

DESCRIPTION OF THE PRIOR ART

The description of the preparation of APA contained in the teachings of Bilow et al in U.S. Pat. No. 3,845,018 involves a large number of expensive and time-consuming steps. Thus Bilow et al in Column 4, lines 41 et seq., teach that an aromatic compound having both nitro and acetyl substitutents is reacted, preferably under reflux, with dimethylformamide and phosphorus oxychloride to convert the acetyl radical to —C(Cl)=CHCHO. The reaction is exothermic, and external cooling is needed to keep it at approximately room temperature. The $\beta$-chloro-substituted aldehyde radical is converted to —C≡CH by refluxing a solution of the compound in p-dioxane and sodium hydroxide. The product is extracted with an organic solvent such as diethylether; the organic solution is dried; the solvent is removed; and the product recovered by vacuum distillation.

Improved techniques over those taught by Bilow et al obviously have to be developed in order to improve the competitive position of the resultant acetylene-terminated polyimides in the marketplace.

One desirable technique to prepare aminophenylacetylene is to first prepare nitrophenylacetylene and then selectively hydrogenate the nitro group. This is a considerably difficult problem, since both the nitro and acetylene groups directly connected to a ring aromatic carbon atom are two of the most reactive groups known for hydrogenation. Undoubtedly the difficulty of selectively hydrogenating a nitro goup in the conjoint presence of an acetylene moiety directly attached to an aromatic ring carbon atom accounts for the literature referring to the use of chemical reducing agents for this purpose. For example, the literature refers to the use of zinc in ammonium hydroxide (A. Burawoy and J. T. Critchley, *Tetrahedron*, No. 5, 340 (1959)); sodium hydrosulfite (see *Organic Syntheses*, Coll. Vol. III, John Wiley & Sons, Inc., New York, NY 1966, p. 69); ammonium sulfite (E. H. Huntress, L. N. Stanley, and A. S. Parker, *J. Am. Chem. Soc.*, 56, 241 (1934)); ferrous sulfate (U.S. Pat. No. 3,845,018 (1974)); stannous chloride (H. M. Woodburn and C. F. Stuntz, *J. Am. Chem. Soc.*, 72, 1361 (1950)); and thiourea dioxide (K. Nakagawa and K. Minami, *Tetrahedron Lett.*, No. 5, 343 (1972)).

Each of the references referred to teaches the effectiveness of the chemical reducing agent in converting 3-nitrophenylacetylene to 3-aminophenylacetylene. The procedures, however, in the referred to literature are generally tedious and unattractive for commercial application. Catalytic hydrogenation with molecular hydrogen is preferable for reasons of economy, safety and flexibility. No satisfactory catalytic method for the selective hydrogenation of aromatic nitro compounds in the conjoint presence of an acetylenic moiety where the acetylenic carbon is directly connected to an aromatic ring carbon atom utilizing a metal oxide catalyst has been reported as yet. Sokol'skii et al, however, studied competitive hydrogenation of phenylacetylene and nitrobenzene over nickel and platinum on alumina and found the addition of hydrogen to acetylene to be nonselective (K. K. Kuzenbaez, K. A. Zhubanov, and B. V. Sokol'skii, *Dokl. Vses. Konf. Khim. Atsetilena*, 4th, 1972, 3, 235; *Chem Abs.*, 79, 77771r (1963)). Reduction of phenylacetylene over palladium on alumina occurs two to three times faster in the presence of nitrobenzene than in its absence. (K. A. Zhubanov, B. V. Sokol'skii, E. P. Maxin, et al, *Zh. Prikl. Khim.*, 47, (8) 1885 (1974); *Chem. Abs.*, 81, 151684z (1974)). Hennion and Barrett hydrogenated propargyl esters of p-nitrobenzoic acid over palladium on barium sulfate and converted the ethynyl group to vinyl without affecting the nitro functionality (G. F. Hennion and S. O. Barrett, *J. Am. Chem. Soc.*, 79, 2146 (1957). Grob and Jenny in U.S. Pat. No. 3,118,946, hydrogenated 2-nitrooctadec-4-yn-1,3-diol over Lindlar catalyst and obtained 2-nitrooctadec-4-en-1,3-diol selectively. It is obvious that the selective hydrogenation of a nitro group in the conjoint presence of the highly reactive acetylenic function where both are directly connected to aromatic ring carbon atoms on the same molecule presents a formidable problem. It is apparent that a wide spectrum of products could be expected since the nitro function, the aromatic ring and the acetylene function can all be partially or completely hydrogenated.

It has now been found in accordance with the invention that nitro aromatic compounds containing at least one nitro group directly connected to an aromatic ring carbon atom, and at least one substituted acetylene moiety directly connected to an aromatic ring carbon through an acetylene carbon, can be selectively reduced using free molecular hydrogen to the corresponding amino aromatic still containing the substituted acetylene moiety by contacting the nitro aromatic compound with a solid catalyst consisting essentially of ruthenium. Preferably the reaction is run in the presence of an inert solvent.

The charge stock for the process of this invention is a nitro aromatic compound containing (i) at least one nitro group directly connected to an aromatic ring carbon atom and (ii) at least one acetylene group directly connected to an aromatic ring carbon atom through one of the acetylene group carbon atoms and which acetylene group has at least three carbon atoms and preferably a hydroxyl group on the carbon atom adjacent to the acetylene group. More preferably, the nitro aromatic compound charge stock has (i) from one to two nitro groups, (ii) from one to two substituted acetylene moieties directly attached through an acetylene carbon atom to aromatic ring carbon atoms, and (iii) from one to two aromatic rings. The aromatic nucleus can be derived from benzene, naphthalene, bibenzyl, diphenyl, diphenyl oxide, diphenyl sulfide, or benzophenone, with the nitro and the acetylene groups being attached to the same or different aromatic rings. The nitro aromatic compound usually has from 9 to 30 carbon atoms and more usually has from 9 to 16 carbon atoms.

Most preferably the nitro aromatic compound charge stock utilized in the process of this invention has the formula:

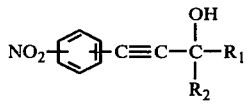

where $R_1$ and $R_2$ can be the same or different and are selected from the group consisting of hydrogen and lower alkyl groups having from 1 to 4 carbon atoms, phenyl, and substituted phenyl, and where $R_1$ and $R_2$ can form a saturated 5- or 6-membered ring.

Suitable specific examples of charge stocks which fall within the scope of this invention include but are not limited to the following materials:

3-(3-nitrophenyl)-2-propyne;
9-nitro-2-(prop-2-yn-3-yl)biphenyl;
5-(3-nitrophenyl)-2-methyl-hex-5-yne;
4-(3-nitrophenyl)-3-butyn-2-ol;
4-(2-nitrophenyl)-3-butyn-2-ol;
4-(4-nitrophenyl)-3-butyn-2-ol;
2-methyl-4-(3-nitrophenyl)-3-butyn-2-ol;
2-methyl-4-(2-nitrophenyl)-3-butyn-2-ol;
2-methyl-(4-nitrophenyl)-3-butyn-2-ol;
2-phenyl-4-(3-nitrophenyl)-3-butyn-2-ol;
2-phenyl-4-(2-nitrophenyl)-3-butyn-2-ol;
2-phenyl-4-(4-nitrophenyl)-3-butyn-2-ol;
3-(3-nitrophenyl)-2-propyn-1-ol;
3-(2-nitrophenyl)-2-propyn-1-ol;
3-(4-nitrophenyl)-2-propyn-1-ol;
3-methyl-5-(3-nitrophenyl)-4-pentyn-3-ol;
3-methyl-5-(2-nitrophenyl)-4-pentyn-3-ol;
3-methyl-5-(4-nitrophenyl)-4-pentyn-3-ol;
1-(3-nitrophenylethynyl)cyclohexanol;
1-(2-nitrophenylethynyl)cyclohexanol;
1-(4-nitrophenylethynyl)cyclohexanol;
1-(3-nitrophenylethynyl)cyclopentanol;
1-(2-nitrophenylethynyl)cyclopentanol;
1-(4-nitrophenylethynyl)cyclopentanol;
2-methyl-4-(2,4-dinitrophenyl)-3-butyn-2-ol;
2-methyl-4-(8-nitro-1-naphthyl)-3-butyn-2-ol;
2-methyl-4-(3-nitro-2-naphthyl)-3-butyn-2-ol;
1,4-bis(2-methyl-3-butyn-2-ol-4-yl)nitrobenzene;
9-nitro-2-[(prop-2-yn-1-ol-3-yl)]biphenyl;
2-nitro-4-(prop-2-yn-1-ol-3-yl)biphenyl;
3-nitro-3'-(prop-2-yn-1-ol-3-yl)diphenyl ether;
4-nitro-4'-(prop-2-yn-1-ol-3-yl)diphenyl ether;
3-nitro-3'-(prop-2-yn-1-ol-3-yl)diphenyl sulfide;
3-nitro-3'-(prop-2-yn-1-ol-3-yl)benzophenone.

The nitro aromatic compound charge stocks described above can be prepared by any suitable procedure, and the method of preparation of these materials forms no part of the present invention. For example, the substituted nitro-aromatic acetylenes can be prepared by reacting nitrophenylacetylene with a ketone in the presence of an alkali metal hydroxide, e.g.

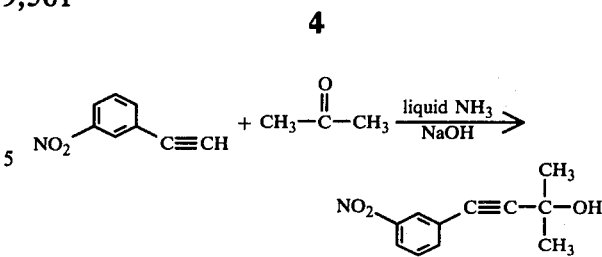

The nitro aromatic charge stocks described above are selectively hydrogenated to produce the corresponding substituted amino aromatic acetylenes, and a list of specific examples would parallel the list of nitro aromatic compounds set forth above except "amino" would replace "nitro" in each compound.

In particular, this invention is concerned with the preparation of novel substituted amino aromatic acetylenes having the formula:

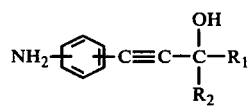

where $R_1$ and $R_2$ can be the same or different and are selected from the group consisting of hydrogen and lower alkyl groups having from 1 to 4 carbon atoms, phenyl, and substituted phenyl, and where $R_1$ and $R_2$ can form a saturated 5- or 6-membered ring.

Preferred among these amino aromatics are those wherein $R_1$ and $R_2$ are methyl; and most preferred is where the amino group is meta to the acetylene moiety.

Specific examples of amino aromatic substituted acetylenes include:

4-(3-aminophenyl)-3-butyn-2-ol;
2-methyl-4-(3-aminophenyl)-3-butyn-2-ol;
2-methyl-4-(2-aminophenyl)-3-butyn-2-ol;
2-methyl-4-(4-aminophenyl)-3-butyn-2-ol;
2-phenyl-4-(3-aminophenyl)-3-butyn-2-ol;
3-(4-aminophenyl)-2-propyn-1-ol;
3-methyl-2-(2-aminophenyl)-4-pentyn-3-ol;
1-(3-aminophenylethynyl)cyclohexanol; and
1-(3-aminophenylethynyl)cyclopentanol.

The preferred substituted amino-aromatic acetylenes of this invention, i.e. those wherein a hydroxyl group is present on the carbon atom adjacent the acetylene group, are intermediates in the preparation of aminophenylacetylene by simple cleavage in the presence of a catalytic amount of base, as shown below, e.g.:

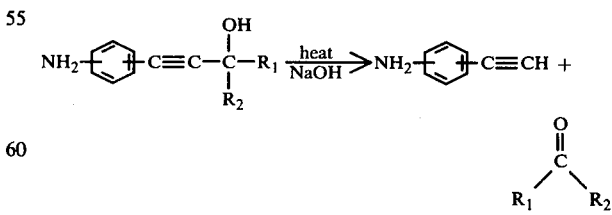

where $R_1$ and $R_2$ are as defined above.

Any alkali metal hydroxide can be utilized to perform the cleavage operation shown above, and such alkali metal hydroxides include: sodium hydroxide, potassium hydroxide and lithium hydroxide.

The substituted amino-aromatic acetylenes are prepared from the corresponding substituted nitro-aromatic acetylenes by the selective hydrogenation of the nitro group using free molecular hydrogen in the contact presence of an unsupported or supported catalyst consisting essentially of ruthenium.

Ruthenium catalysts, supported and unsupported, are known and available commercially. The method of preparation of the ruthenium catalyst is therefore not critical, but it is important that the ruthenium be converted to an active species before being utilized in the subject reaction. By "activated ruthenium" is meant a species of ruthenium which will promote the selective hydrogenation reactions of this invention, and this "activated" ruthenium is believed to be ruthenium in the zero valent form. As will be shown below, a catalyst consisting essentially of oxidized ruthenium on an alumina support is inactive for the subject reaction even though the subject reaction is operated under hydrogenation reduction conditions. The ruthenium oxide catalyst is perhaps inactive due to the mildness of the reaction conditions of this invention (70° C.), and perhaps the presence of an organic liquid phase in the reaction zone. When the same ruthenium oxide catalyst is prereduced in hydrogen (no liquid phase) at 350° C. for three hours, or at 200° C. for one hour in the added presence of water, the ruthenium is converted to an active form. Apparently insufficient reduction of the ruthenium oxide occurs under very mild conditions in the presence of an organic liquid phase to activate the catalyst. It is a simple matter for one skilled in the art to determine the degree of reduction necessary to activate the ruthenium knowing the above. It is believed the reduction results in a conversion of at least a portion of the ruthenium to the zero valent form, although some suboxides of ruthenium may be present, or there may be mixtures of ruthenium in the zero valent form and ruthenium suboxides.

The ruthenium can be employed unsupported but, due to the expensive nature of ruthenium, is suitable and preferably distended or dispersed substantially uniformly over a catalyst support by techniques which are well known to those having ordinary skill in the art. For example, the ruthenium can be deposited from a salt solution, usually aqueous, onto the support, which is then dried; and the salt is thereafter decomposed to yield the activated ruthenium, such as by heating in the presence of hydrogen or calcining followed by reduction in the presence of $H_2$ at elevated temperatures. Suitable ruthenium salts include, without limitation: barium perruthenate, sodium perruthenate, and the like; ruthenates such as magnesium, strontium, calcium, silver, barium and sodium ruthenates; perruthenates such as sodium and potassium perruthenates and the like; ruthenium halides such as ruthenium dichloride, ruthenium trichloride, ruthenium tetrachloride, ruthenium pentafluoride, and the like; and chloro salts of ruthenium such as potassium chloroperruthenate. Another technique is to prepare barium ruthenate and to physically admix the barium ruthenate by ball-milling with a support such as gamma-alumina, followed by a reduction of the final product to produce an activated ruthenium catalyst. This technique is described, for example, in U.S. Pat. No. 3,907,968 to Kobylinski et al, issued Sept. 23, 1975.

The catalyst supports which can be employed are any of those which are well-known, non-catalytic-cracking type supports such as those which are used for hydrogenation type reactions in the petroleum industry. Specific examples of suitable catalyst supports include: carbon, alumina (including activated alumina), silica (including kieselguhr), and synthetic gels, titanium dioxide, calcium carbonate, barium sulfate, bentonite, and the like. The preferred supported catalysts have a ruthenium metal content from 0.01 weight percent to about 10 percent by weight of the final catalyst, preferably from 0.4 to 7 weight percent of the catalyst calculated as ruthenium, and most preferably from 0.5 to 5 weight percent.

The selective hydrogenation reaction of this invention can be run neat by contacting the charge stock in the liquid phase along with free molecular hydrogen with an activated ruthenium catalyst under relatively mild reaction conditions including a temperature from about 20° to 120° C. The charge stocks are, however, highly reactive as they contain both nitro and acetylene functions; and for safety reasons, it is preferred to operate the reaction in the presence of an inert solvent, which functions primarily as a heat control medium. By better heat control, side reactions such as polymerization, condensation and hydrolysis are inhibited.

The type and amount of solvent are not critical, but it is preferred to employ a solvent which is miscible with the water of reaction so that separate phases are not formed during the selective reduction reaction. This is especially important in batch phase operations using powdered catalysts which tend to clump in the presence of free water and thus prematurely stop the reaction. From the above it is obvious that the amount of solvent to employ is that preferably sufficient to maintain a single liquid phase reaction system. Obviously the solvent must be miscible with the charge stock and must also resist reaction with hydrogen under the mild conditions of this invention. Usually the solvent-to-charge stock weight ratio is from 1:1 to 200:1, and more usually is from 4:1 to 20:1.

Examples of suitable solvents include but are not meant to be limited to: aliphatic alcohols having from 1 to 5 carbon atoms, such as methanol, ethanol, propanol, isopropanol and pentanol; organic esters having from 3 to 6 carbon atoms, such as ethyl acetate, methyl acetate; low molecular weight ethers, such as methylethyl ether, diethyl ether, methylpropyl ether, tetrahydrofuran and p-dioxane; low molecular weight organic acids having from 2 to 5 carbon atoms, such as acetic acid, propionic acid; and toluene.

The selective reduction reactions of this invention can be operated using, for example, a batch or continuous process. In a batch process, the catalyst can be in any suitable form, such as powdered, pelleted, extruded, etc. The weight ratio of charge stock to catalyst in a batch process is usually 1:1 to 1000:1, but this ratio is not critical. In a continuous-type operation, the catalyst can be in a pelleted or extruded form, which is normal for use in a fixed-bed type of operation where the charge material can suitably be passed downflow in liquid phase through the catalyst zone or upflow in a flooded bed type of operation. The free molecular hydrogen necessary for the reduction reaction can be passed concurrently with the charge stock or can enter the reaction zone countercurrent to the charge stock.

The reaction conditions are mild and include a temperature from 20° to 120° C., preferably 25° to 80° C. The reaction rate below 20° C. is too low to be of commercial significance, while temperatures above about 120° C. tend to promote undesired side reactions such as polymerization and hydrogenation of the acetylene groups.

The reaction pressure is not critical, and suitable reaction pressures include atmospheric to 150 atmospheres, preferably 2 atmospheres to 10 atmospheres. The reaction is operated, of course, in the presence of free molecular hydrogen, which at atmospheric pressure can be bubbled through the reaction mixture. The reaction is preferably operated at elevated hydrogen partial pressures of from 2 to 10 atmospheres (202 to 1010 kPa). The reaction time is likewise not critical and is a function of many variables including the type of charge stock and the reaction conditions. Usually the reaction times are from 10 minutes to 100 hours; more usually the reaction time is from 30 minutes to 10 hours.

It has been found that the nitro group on the substituted nitro-aromatic acetylene charge stocks of this invention is selectively reduced at high conversion levels to give unexpectedly high yields of the desired substituted amino aromatic acetylenes. The process of this invention can be operated within the range of conditions set forth above to provide weight percent conversions of the nitro aromatic compound charge stocks from 70 to 100 percent, although, obviously, lower conversions can occur. The selectivities to the production of the desired corresponding amino aromatics still containing the acetylene group are usually over 70 percent and can be from 90 to 100 percent, even at the higher conversion levels.

The product recovery is not difficult and can suitably be achieved by simple vacuum or steam distillation or by fractional crystallization to separate the product from unreacted charge stock. Obviously care must be taken in the distillation of the products (or other recovery technique) from the realization that the products contain an acetylene function. After the product is removed from the reaction zone, it has been found that the catalyst can be reused directly a number of times without prereduction, regeneration, or other treatment of the catalyst.

The invention will be further described with reference to the following experimental work.

EXPERIMENTAL WORK

In all of the working Examples, the substituted nitro aromatic acetylene charge stock was 2-methyl-4-(3-nitrophenyl)-3-butyn-2-ol.

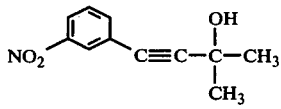

Unless otherwise noted, a batch-type reaction was employed, as follows:

(1) The 2-methyl-4-(3-nitrophenyl)-3-butyn-2-ol was dissolved in isopropanol or toluene, which were used as the solvents.

(2) The catalyst was added, and the mixture placed into a standard 500-ml Parr hydrogenation bottle.

(3) The system was purged with hydrogen.

(4) The desired operating temperature was adjusted, and the bottle pressured with free molecular hydrogen to 60 psig (414 kPa) and maintained in the stipulated pressure range by periodic injection of measured amounts of additional hydrogen.

(5) The reaction was allowed to proceed until the theoretical amount of hydrogen was consumed to convert the $-NO_2$ groups in the charge stock to $-NH_2$ and water. (The hydrogen consumed was measured either by pressure drop or by gas-liquid chromatography of aliquots.)

(6) After the reaction was deemed complete, the reaction mixture was allowed to cool to room temperature and the mixture was then filtered through a glass frit to remove the catalyst.

(7) The liquid product was then stripped of solvent on a rotary evaporator to give a tan solid (melting point 114° to 116° C.) which was then subject to gas chromatography which showed onl the presence of 2-methyl-4-(3-aminophenyl)-3-butyn-2-ol.

(8) The solid product (which contained traces of solvent) was recrystallized from toluene to yield cream-colored needles having a melting point of 117° to 118° C. The cream-colored needles were shown to have a molecular weight of 175 by mass spectroscopy. The fragmentation pattern showed strong ions at $(M-18)^+$ indicating loss of water and at $(M-58)^+$ indicating loss of acetone from the parent ion. The nuclear magnetic resonance spectrum $(CDCl_3)$ was delta 7.2–6.6 (m, 4H), 4.6–3.8 (broad resonance, 3H, exchanges with $D_2O$), 1.56 (S, 6 H).

The elemental analysis of the cream-colored needles was as follows: C, 75.63; H, 7.38; N, 7.48. (Theoretical is C, 75.40; H, 7.48; and N, 7.99.)

From the above it was determined that the product has the molecular formula: $C_{11}H_{13}NO$.

In all of the working Examples in this specification, the term "conversion" shall mean weight percent of 2-methyl-4-(3-nitrophenyl)-3-butyn-2-ol converted to all products; and "selectivity" shall mean the weight of 2-methyl-4-(3-aminophenyl)-3-butyn-2-ol isolated from the reaction product divided by the weight of 2-methyl-4-(3-aminophenyl)-3-butyn-2-ol theoretically expected.

EXAMPLE 1

Gamma-alumina was ground to pass 100-mesh U.S. standard sieve, and the powdered alumina was calcined at 540° C. for 10 hours. The calcined gamma-alumina was then impregnated by the incipient wetness technique with an aqueous solution containing a sufficient amount of ruthenium trichloride hydrate to result in 5% by weight ruthenium (calculated as the metal) after calcination. The material was then oven-dried at 120° C. for 24 hours before a final calcination in air for 10 hours at 540° C.

EXAMPLE 2

The catalyst of Example 1 was utilized for the hydrogenation of 2-methyl-4-(3-nitrophenyl)-3-butyn-2-ol at 70° C., a hydrogen pressure of 50 to 60 psig (345–414 kPa) for a reaction time of 2.5 hours using toluene as the solvent. Analysis of the product indicated that no reaction had occurred. The results of this Example are shown in Table 1 below.

EXAMPLE 3

The catalyst of Example 1 was activated by contacting a portion of the catalyst from Example 1 with hydrogen in the presence of water at 1000 psig (6.9 MPa) for one hour at 200° C.

EXAMPLE 4

Example 2 was repeated except using the activated catalyst of Example 3, and after a reaction time of 0.58 hours, 100% of the charge stock was converted to the corresponding amino aromatic acetylene in a 100% selectivity. The results of this run are summarized on Table 1 below.

A comparison of Examples 2 and 4 indicates that some reduction of the ruthenium oxide catalyst must occur to achieve an activated ruthenium catalyst.

EXAMPLE 5

A portion of the catalyst from Example 1 was pretreated the same as in Example 3, except no hydrogen was present.

EXAMPLE 6

Example 2 was repeated except using the activated catalyst of Example 5, and after a reaction time of two hours, only 1% of the charge stock was converted. The results are summarized in Table 1 below.

EXAMPLE 7

A portion of the catalyst prepared as in Example 1 was pretreated by heating the catalyst at 350° C. under an atmosphere of hydrogen for three hours in the absence of water.

EXAMPLE 8

Example 1 was repeated using the preactivated catalyst of Example 7, and a 79% conversion of the charge stock was observed, with a 100% selectivity to the corresponding amino aromatic after a reaction time of 0.58 hours. The results are summarized in Table 1 below.

When Examples 1 through 8 are compared, it is observed that some reduction of the ruthenium oxide is required to obtain activation of the ruthenium. Apparently activation in the presence of hydrogen plus water (Ex's 3 and 4) gives better results than activation in hydrogen alone (Ex's 7 and 8), albeit the difference in activity could be and probably is the result of the increased hydrogen pressure activation utilized in Example 3.

A series of runs was made using isopropanol as the solvent and utilizing a ruthenium catalyst purchased from ROC/RIC (Research Organic/Inorganic Chemicals Company) and these purchased ruthenium catalysts were known to have been pretreated with a stream of hydrogen at 200° to 300° C. before receipt.

EXAMPLE 9

In the run for this Example, the purchased ROC/RIC ruthenium catalyst was utilized for the hydrogenation of 2-methyl-4-(3-nitrophenyl)-3-butyn-2-ol at 50° C. and a hydrogen pressure of 50-60 psig (345-414 kPa) until the stoichiometric drop in hydrogen pressure was observed. The conversion and selectivity were both 100%. The results are shown in Table 1 below.

EXAMPLES 10-13

A series of Examples (10-13) were then run, repeating Example 5, except successively using the catalyst from the prior Example to determine if the activity of the catalyst could be maintained. The results of these Examples, which are summarized in Table 1 below, illustrate that the catalyst activity did not decrease substantially with time.

EXAMPLE 14

In the run for this Example, the used catalyst from Example 13 was employed without any regeneration of the catalyst occurring. The run was substantially the same as the run for Examples 9-13 except 20.5 grams of the nitroaromatic charge stock were employed in place of the 2.1 grams earlier utilized. Thus the ratio of charge stock to catalyst was approximately ten times greater. The reaction temperature was increased to 70° C. (in place of 50° C. used in Ex's 9-13), and the reaction time was found to increase to 24 hours in order to obtain substantially complete conversion. Despite the long reaction time, the selectivity to the formation of the desired substituted aminophenylacetylene was 100%. This run is also summarized in Table 1 below.

EXAMPLE 15

In the run for this Example, the catalyst was five percent ruthenium on a charcoal support, also purchased from ROC/RIC and prereduced with hydrogen. After 21 hours of reaction at 20° C., the conversion was 99%, and the selectivity to the desired substituted aminophenylacetylene was 95%. This run is also summarized in Table 1, and a comparison of this catalyst and those of prior Examples illustrates that different catalyst supports can be used.

EXAMPLE 16

Example 9 was repeated, except no solvent was employed, and the reaction temperature was increased to 70° C. After 4½ hours, the conversion was 90 weight percent; selectivity to the substituted aminophenylacetylene was 100%. This run is also summarized in Table 1 below and shows that a solvent is not essential to the reaction.

EXAMPLE 17

Example 9 was repeated except the reaction was purposely allowed to exceed the stoichiometric pressure drop of hydrogen to demonstrate the need to monitor the reaction closely. As a result, 100% of the nitro compound charge stock was converted, but the selectivity to the formation of the aminophenyl butynol was only 58%, with the remainder being further hydrogenated products including 2-methyl-4-(3-aminophenyl)-3-buten-2-ol (22%) and 2-methyl-4-(3-aminophenyl)-butan-2-ol (15%). This run is also summarized in Table 1.

EXAMPLE 18

In the run for this Example, the catalyst was prepared in accordance with Example 3 above, except the amount of ruthenium trichloride hydrate used was sufficient to result in only 0.5 weight percent ruthenium on the final catalyst (rather than the 5% in Example 3).

EXAMPLE 19

Example 9 was repeated except using the catalyst of Example 18; a reaction temperature of 70° C. for a reaction time of only 0.33 hours. The conversion was found to be 56% with a 100% selectivity to the desired 2-methyl-4-(3-aminophenyl)-3-butyn-2-ol. The results are summarized in Table 1 below.

Example 19 illustrates that catalysts containing amounts of ruthenium as low as 0.5% (or lower) can suitably be employed without ill effect on selectivity.

EXAMPLE 20

In the run for this Example, Raney nickel (purchased from W. R. Grace Co.) was employed as the catalyst at ambient temperatures, and after only 15 minutes the conversion was 100% with 0% selectivity to the desired amino compound. This run is also summarized in Table 1.

EXAMPLE 21

In the run for this Example, the catalyst was nickel 0104 (purchased from the Harshaw Co.), and after three hours of operation at 50° C., zero percent conversion of the charge stock was observed (no hydrogen pressure drop). The results of this run are shown in Table 1 below.

Examples 20 and 21 illustrate that another Group VIII metal (nickel) has no selectivity (Ex. 20) or activity (Ex. 21) for the subject reaction.

ylene moiety to the corresponding double and single bonds occurred along with some reduction of the nitro group. Selectivity to individual compounds found was:

| | |
|---|---|
| 2-methyl-4-(3-aminophenyl)-3-buten-2-ol | (45%) |
| 2-methyl-4-(3-aminophenyl)-butan-2-ol | (35%) |
| 2-methyl-4-(3-nitrophenyl)-3-buten-2-ol | (14%) |
| 2-methyl-4-(3-nitrophenyl)-butan-2-ol | ( 6%) |

This run is summarized in Table 2 below.

EXAMPLE 24

In the run for this Example, a catalyst was prepared in a similar fashion to Example 22 above, except containing only 500 ppm of palladium in addition to the 5 weight percent ruthenium.

EXAMPLE 25

Example 2 was repeated except using the catalyst of Example 24, and, after 0.5 hours, 57% of the charge stock was converted with a selectivity of 53% to the desired 2-methyl-4-(3-aminophenyl)-3-butyn-2-ol. Also found were:

| | |
|---|---|
| 2-methyl-4-(3-aminophenyl)-3-buten-2-ol | (13%) |
| 2-methyl-4-(3-aminophenyl)-buutan-2-ol | (31%) |
| 2-methyl-4-(3-nitrophenyl)-3-buten-2-ol | ( 3%) |

This run is summarized in Table 2 below.

TABLE 1
HYDROGENATION OF 2-METHYL-4-(3-NITROPHENYL)-3-BUTYN-2-OL

| Ex. No. | Wt Substrate, grams | Solvent, ml | Catalyst Type | Catalyst Grams | Temp. °C | Pressure psig | Time, hrs. | % Conv. | % Selec. |
|---|---|---|---|---|---|---|---|---|---|
| 2 | 2.1 | Toluene (150) | 5% Ru oxide on Al$_2$O$_3$ (Ex.1 cat.) | 1 | 70 | 50–60 | 2.25 | 0 | 0 |
| 4 | 2.1 | Toluene (150) | 5% Ru on Al$_2$O$_3$ (Ex.3 cat.) | 1 | 70 | 50–60 | 0.58 | 100 | 100 |
| 6 | 2.1 | Toluene (150) | 5% Ru on Al$_2$O$_3$ (Ex.5 cat.) | 1 | 70 | 50–60 | 2.0 | 1 | 100 |
| 8 | 2.1 | Toluene (150) | 5% Ru on Al$_2$O$_3$ (Ex.7 cat.) | 1 | 70 | 50–60 | 0.58 | 79 | 100 |
| 9 | 2.1 | Isopropanol (150) | 5% Ru on Al$_2$O$_3$ | 1 | 50 | 50–60 | 3.5[b] | 100 | 100 |
| 10 | 2.1 | Isopropanol (100) | 5% Ru on Al$_2$O$_3$ | 1 | 50 | 50–60 | 2.5 | 95 | 95[c] |
| 11 | 2.1 | Isopropanol (150) | 5% Ru on Al$_2$O$_3$ | 1 | 50 | 50–60 | 4.58[b] | 100 | 100 |
| 12 | 2.1 | Isopropanol (150) | 5% Ru on Al$_2$O$_3$ | 1 | 50 | 50–60 | 4.25[b] | 100 | 100 |
| 13 | 2.1 | Isopropanol (150) | 5% Ru on Al$_2$O$_3$ | 1 | 50 | 50–60 | 3.50 | 99 | 98 |
| 14 | 20.5 | Isopropanol (200) | 5% Ru on Al$_2$O$_3$ | 1 | 70 | 40–60 | 24[b] | 100 | 100 |
| 15 | 2.1 | Isopropanol (150) | 5% Ru on charcoal | 0.5 | 20 | 35–60 | 21 | 99 | 95[c] |
| 16 | 4.1 | No solvent | 5% Ru on alumina | 1 | 70 | 50–60 | 4.5 | 90 | 100 |
| 17 | 2.1 | Isopropanol (150) | 5% Ru on alumina | 1 | 50 | 50–60 | 4.25 | 100 | 58[d] |
| 19 | 2.1 | Isopropanol (150) alumina | 0.5% Ru on alumina | 10 | 70 | 50–60 | 0.33 | 56 | 100 |
| 20 | 4.1 | Isopropanol (150) | Raney nickel | 3 | 20 | 50–60 | 0.25 | 100 | 0[e] |
| 21 | 2.1 | Isopropanol (150) | Ni 0104 | 1 | 50 | 60 | 3 | 0 | — |

[a]"Substrate" means 2 methyl-4-(3-nitrophenyl)-3-butyn-2-ol.
[b]Reaction stopped after stoichiometric pressure drop.
[c]Traces of azo and azoxy reduction intermediates present.
[d]Also present: 2 Me-4-(3-aminophenyl)-3-buten-2-ol (22%) and 2 Me-4-(3-aminophenyl)-butan-2-ol (15%)
[e]Quantitive conversion to 2-Me-4-(3-aminophenyl)-butan-2-ol.

EXAMPLE 22

In the run for this Example, a catalyst was prepared as in Example 3 except a sufficient amount of palladium chloride was employed to coimpregnate 2000 ppm by weight palladium in addition to the 5 weight percent ruthenium onto the support.

EXAMPLE 23

Example 2 was repeated using the catalyst of Example 22 and, after 0.67 hours, 48% of the charge stock was converted. No trace of the desired amino aromatic acetylene was found. Preferential reduction of the acet- Examples 23 and 25 demonstrate the need for high purity of the ruthenium used in this invention. Example 25, corresponding to the use of ruthenium of about 99% purity, already shows almost 50% loss of selectivity. Example 23, corresponding to the use of ruthenium of about 96% purity, shows complete loss of selectivity.

TABLE 2
EFFECT OF PURITY OF RUTHENIUM ON THE HYDROGENATION OF 2-METHYL-4-(3-NITROPHENYL)-3-BUTYN-2-OL

| Ex. No. | Sub- strate,[a] grams | Solvent (ml) | Catalyst Type | Catalyst Grams | Temp °C | Pres- sure psig | Time hrs | % Conv. | % Selec. |
|---|---|---|---|---|---|---|---|---|---|
| 23 | 2.1 | Toluene (150) | 5% Ru/Al$_2$O$_3$ containing 2000 ppm Pd (Cat. of Ex.22) | 1 | 70 | 50–60 | 0.67 | 48 | 0[b] |
| 25 | 2.1 | Toluene (150) | 5% Ru/Al$_2$O$_3$ containing 500 ppm Pd (Cat. of Ex.24) | 1 | 70 | 50–60 | 0.50 | 57 | 53[c] |

[a]"Substrate" means 2-methyl-4-(3-nitrophenyl)-3-butyn-2-ol.
[b]Also present:
2-Me-4-(3-aminophenyl)-3-buten-2-ol (45%) and
2-Me-4-(3-aminophenyl)-butan-2-ol (35%) and
2-Me-4-(3-nitrophenyl)-3-buten-2-ol (14%) and
2-Me-4-(3-nitrophenyl)-butan-2-ol ( 6%).
[c]Also present:
2-Me-4-(3-aminophenyl)-3-buten-2-ol (13%) and
2-Me-4-(3-aminophenyl)-butan-2-ol (31%) and
2-Me-4-(3 nitrophenyl)-3-buten-2-ol ( 3%).

EXAMPLE 26

Example 19 above was repeated, except utilizing 10 grams of the 0.5% ruthenium on alumina catalyst purchased from Strem Company; and after 2.33 hours of reaction time, a conversion of 68% was obtained. Product analyses by gas liquid chromatography showed that only 11% selectivity to the desired substituted aminophenylacetylene was obtained. A complete breakdown of the product is as follows:

| | |
|---|---|
| 2-methyl-4-(3-aminophenyl)-3-buten-2-ol | ( 4%) |
| 2-methyl-4-(3-nitrophenyl)-3-buten-2-ol | (68%) |
| 2-methyl-4-(3-nitrophenyl)-butan-2-ol | (16%) |

It appears the purchased catalyst used in Example 24 had impurities of some nature which resulted in a reduced selectivity (a 0.5% pur ruthenium catalyst gave 100% selectivity in Example 19 above). Because of the low metal levels, analysis for impurities was beyond the scope of the techniques employed (atomic adsorption).

EXAMPLE 27

In the run for this Example, a BaRuO$_3$-gamma-alumina catalyst was prepared in accordance with the teachings of Example 12 in U.S. Pat. No. 3,097,968. The resulting catalyst was activated by treatment at 1000 psig (6.9 MPa) with hydrogen at 200° C. in the presence of water for one hour. Example 9 was repeated except using the BaRuO$_3$-gamma-alumina catalyst described immediately above, and after 1.75 hours of reaction time, the conversion of the charge stock was 85%, with a selectivity of about 90% to the desired product.

EXAMPLE 28

2 grams of 2-methyl-4-(3-aminophenyl)-3-butyn-2-ol were dissolved in 15 ml of toluene containing one pellet (0.1 gram) of sodium hydroxide which had been crushed to a powder. The mixture was charged to a 100 ml, round-bottom flask equipped with a Dean-Stark trap and condenser. The mixture was refluxed for one hour, and the acetone byproduct was removed periodically through the Dean-Stark trap. The reaction product was then cooled, and the mixture filtered to remove particles of caustic. After the solvent was stripped, a quantitative yield of 3-aminophenylacetylene (1.4 grams) of greater than 98% purity as analyzed by gas chromatograhy was obtained.

Resort may be had to the variations and modifications as fall within the spirit of the invention and the scope of the appended claims.

We claim:

1. A process for the production of an aromatic amino compound containing an acetylene group having at least three carbon atoms and where the acetylene group is directly connected to an aromatic ring carbon atom which comprises:

contacting a charge stock comprising an aromatic nitro compound containing (i) at least one nitro group directly connected to an aromatic ring carbon atom and (ii) at least one acetylene group having at least three carbon atoms and wherein the acetylene group is directly connected to an aromatic ring carbon atom in the liquid phase with a solid catalyst consisting essentially of ruthenium and in the added presence of free molecular hydrogen under hydrogenation conditions.

2. A process according to claim 1 wherein the reaction occurs in the added presence of an inert solvent.

3. A process according to claim 2 wherein the inert solvent is an organic oxygen containing compound.

4. A process in accordance with claim 2 wherein the organic solvent is selected from the group consisting of alcohols having from 1 to 5 carbon atoms, esters having from 3 to 6 carbon atoms; tetrahydrofuran; p-dioxane; organic acids having from 2 to 5 carbon atoms; and toluene.

5. A process in accordance with claim 4 wherein the aromatic nitro compound charge stock has a single aromatic ring.

6. A process in accordance with claim 1 wherein said charge stock contains an hydroxyl group on the carbon atom adjacent to the acetylene group and the hydrogenation reaction occurs at a temperature from 20° to 120° C.

7. A process in accordance with claim 6 wherein said aromatic nitro compound has the formula:

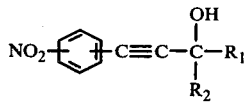

where $R_1$ and $R_2$ can be the same or different and are selected from the group consisting of hydrogen and lower alkyl groups having from 1 to 4 carbon atoms, phenyl, and substituted phenyl, and where $R_1$ and $R_2$ can form a saturated 5- or 6-membered ring.

8. A process in accordance with claim 7 wherein $R_1$ and $R_2$ are both methyl.

9. A process in accordance with claim 8 wherein the nitro compound is 2-methyl-4-(3-nitrophenyl)-3-butyn-2-ol.

10. A process in accordance with claim 1 wherein said ruthenium is distended on a support.

11. A process in accordance with claim 10 wherein the amount of ruthenium distended on said support is from 0.01 to 10 weight percent of the final catalyst.

12. A process in accordance with claim 11 wherein said catalyst support is selected from the group consisting of carbon, alumina, kieselguhr, silica, titanium dioxide, calcium carbonate, barium sulfate and bentonite.

13. A process in accordance with claim 12, which process is operated in the added presence of an organic solvent selected from the group consisting of alcohols having from 1 to 5 carbon atoms; esters having from 3 to 6 carbon atoms; tetrahydrofuran; p-dioxane; organic acids having from 2 to 5 carbon atoms; and toluene.

14. A process in accordance with claim 13 wherein the nitro organic compound has the formula:

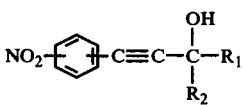

where $R_1$ and $R_2$ can be the same or different and are selected from the group consisting of hydrogen and lower alkyl groups having from 1 to 4 carbon atoms, phenyl, and substituted phenyl, and where $R_1$ and $R_2$ can form a saturated 5- or 6-membered ring.

15. A process in accordance with claim 14 wherein the support is alumina.

16. A process in accordance with claim 15 wherein the nitro-organic compound is 2-methyl-4-(3-nitrophenyl)-3-butyn-2-ol.

17. A process in accordance with claim 10 wherein the catalyst is prepared by uniformly dispersing the ruthenium from an aqueous ruthenium salt solution onto said support; drying the catalyst; and contacting the dried catalyst with hydrogen to convert at least a portion of the ruthenium salt to ruthenium metal.

18. A process in accordance with claim 17 wherein the ruthenium salt is ruthenium chloride hydrate and the method of uniformly dispersing the ruthenium is by the incipient wetness technique.

19. A process in accordance with claim 10 wherein the catalyst is prepared by uniformly dispersing the ruthenium from an aqueous ruthenium salt solution onto said support; drying said catalyst; calcining said catalyst at an elevated temperature to convert the ruthenium salt to the oxide form; followed by contacting with hydrogen to convert at least a portion of the ruthenium oxide to a reduced state.

20. A process in accordance with claim 19 wherein the contacting with hydrogen occurs in the added presence of water.

21. A process in accordance with claim 20 wherein the ruthenium salt is ruthenium chloride hydrate and the method of uniformly dispersing the ruthenium is by the incipient wetness technique.

22. A process in accordance with claim 1 wherein the resultant aromatic amino compound is converted to an amino aromatic acetylene by reacting said aromatic amino compound with an alkali metal hydroxide in the presence of an aromatic solvent.

23. A process in accordance with claim 22 wherein the alkali metal hydroxide is sodium hydroxide.

24. A process in accordance with claim 23 wherein the aromatic solvent is toluene.

25. A process in accordance with claim 24 wherein said reaction is operated at reflux conditions.

26. A process for the preparation of an aminophenylacetylene by the selective reduction of the nitro group in a nitrophenylacetylene having the formula:

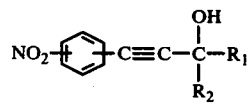

where $R_1$ and $R_2$ can be the same or different and are selected from the group consisting of hydrogen and lower alkyl groups having from 1 to 4 carbon atoms, phenyl, and substituted phenyl, and where $R_1$ and $R_2$ can form a saturated 5- or 6-membered ring which comprises:

contacting said nitrophenylacetylene in the liquid phase in the presence of an inert organic solvent with a catalyst consisting essentially of ruthenium and in the added presence of free molecular hydrogen under hydrogenation conditions including a temperature from 20° to 150° C.;

separating the resultant aminophenyl substituted acetylene from the reaction product;

reacting said separated aminophenyl substituted acetylene with an alkali metal hydroxide in the presence of an aromatic solvent to produce aminophenylacetylene.

27. A process in accordance with claim 265 wherein the nitro group on the nitrophenylacetylene is in the meta position.

28. An aromatic amino compound having the formula:

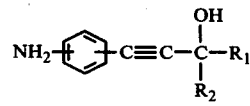

where $R_1$ and $R_2$ can be the same or different and are selected from the group consisting of hydrogen and lower alkyl groups having from 1 to 4 carbon atoms, phenyl, and substituted phenyl, and where $R_1$ and $R_2$ can form a saturated 5- or 6-membered ring.

29. An aromatic amino compound according to claim 28 wherein $R_1$ and $R_2$ are both methyl.

30. 2-methyl-4-(3-aminophenyl)-3-butyn-2-ol.

* * * * *